United States Patent
Amemiya et al.

(10) Patent No.: US 7,368,612 B2
(45) Date of Patent: May 6, 2008

(54) METHOD OF PRODUCING HIGH-PURITY HYDROXYPIVALALDEHYDE AND/OR DIMER THEREOF

(75) Inventors: Junichi Amemiya, Okayama (JP); Masafumi Watanabe, Okayama (JP); Ikutaro Kuzuhara, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/498,871

(22) Filed: Aug. 4, 2006

(65) Prior Publication Data

US 2007/0032682 A1    Feb. 8, 2007

(30) Foreign Application Priority Data

Aug. 8, 2005   (JP)  ............................. 2005-229171

(51) Int. Cl.
   *C07C 45/75*  (2006.01)
(52) U.S. Cl. ................................................. 568/461
(58) Field of Classification Search ................ 568/461
   See application file for complete search history.

(56) References Cited

U.S. PATENT DOCUMENTS 4,036,888 A    7/1977    Couderc et al.

FOREIGN PATENT DOCUMENTS

| JP | 19680046758 | 7/1968 |
| JP | 51-68514 | 6/1976 |
| JP | 61-18741 | 1/1986 |
| JP | 01-299239 | 12/1989 |
| JP | 06-029206 | 2/1994 |
| JP | 07-215904 | 8/1995 |
| JP | 2000-026356 | 1/2000 |
| JP | 2005-029563 | 2/2005 |

OTHER PUBLICATIONS

European Search Report, for Application No. EP 06 11 8168, dated Nov. 20, 2006.

*Primary Examiner*—Sikarl A. Witherspoon
(74) *Attorney, Agent, or Firm*—Antonelli, Terry, Stout & Kraus, LLP.

(57) ABSTRACT

The present invention provides a method of producing high-purity hydroxypivalaldehyde and/or dimer thereof, including: reacting isobutyl aldehyde with formaldehyde in a presence of a basic catalyst; distilling a low boiling point component including unreacted isobutyl aldehyde to obtain an aqueous solution; adding a diluent to the aqueous solution; cooling the aqueous solution to crystallize the hydroxypivalaldehyde and/or the dimer thereof; and subjecting the aqueous solution to a solid-liquid separation, followed by washing with an organic solvent and/or water, in which the diluent and a basic compound are added to the aqueous solution containing the hydroxypivalaldehyde and/or the dimer thereof obtained by distilling the low boiling point component off so that a concentration of the hydroxypivalaldehyde and/or the dimer becomes 5 to 23% by mass, the concentration of formaldehyde becomes 0.2 to 2.5% by mass, and a pH value becomes 5.0 or more, the solution is crystallized at a temperature of 20 to 45° C. and subjected to the solid-liquid separation. In this method, handling of a high-viscosity slurry and carrying out any complicated operation such as regeneration of an ion exchange resin are not required, so the high-purity HPA and/or the dimer thereof can be obtained in high yield with an energetically advantageous manner.

14 Claims, No Drawings

METHOD OF PRODUCING HIGH-PURITY HYDROXYPIVALALDEHYDE AND/OR DIMER THEREOF

BACKGROUND OF THE INVENTION

1. Field of the Invention

The present invention relates to a method of producing hydroxypivalaldehyde and/or a dimer thereof by subjecting isobutyl aldehyde to reaction with formaldehyde. More specifically, the present invention relates to a method of efficiently and simply producing high-purity hydroxypivalaldehyde and/or the dimer thereof by separating the hydroxypivalaldehyde and/or the dimer thereof from a reaction solution by a crystallization process.

2. Description of the Prior Art

In general, hydroxypivalaldehyde (3-hydroxy-2,2-dimethyl propanal, hereinafter referred to as HPA) is synthesized by an aldol condensation reaction of isobutyl aldehyde with formaldehyde in the presence of a basic catalyst. The aldol condensation reaction can proceed either in acidic conditions or basic conditions. However, HPA has a carbonyl group and a hydroxyl group in a single molecule thereof, so the condensation of dimers into tetramers occurs under acidic conditions. Thus, the aldol condensation reaction is generally carried out under basic conditions as mentioned above (Japanese Patent Application Laid-Open No. 07-215904 and Japanese Patent Application Laid-Open No. 2000-26356).

After the reaction is completed, low boiling point components, such as unreacted isobutyl aldehyde and formaldehyde, are distilled off to thereby obtain an HPA-containing aqueous solution. HPA has been often used as a synthetic intermediate of an organic compound such as neopentylglycol or spiroglycol, and such the liquid resulting from the reaction is often used in subsequent steps without being purified (Japanese Patent Application Laid-Open No-01-299239 and Japanese Patent Application Laid-Open No. 2005-29563).

As for HPA, there is an equilibrium relationship between a monomer and a dimer as represented by the chemical formula (I) (Journal of the Chemical Society, Perkin Transactions II, vol. 3, page 189-192, 1978). HPA obtained as a crystal by crystallization and purification is a dimer. Japanese Patent Application Laid-Open No. 01-299239 and the like disclose that the dimer is as reactive as the monomer.

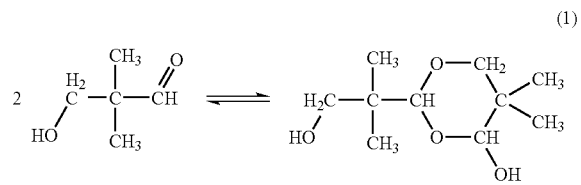

(1)

In addition, methods of obtaining high-purity HPA are disclosed in Japanese Patent Application Laid-Open No. 51-68514 and Japanese Patent Publication No. 06-29206, in which the HPA-containing aqueous solution is diluted with the addition of water and then purified by crystallization, followed by solid-liquid separation to thereby obtain the high-purity HPA.

In other words, Japanese Patent Application Laid-Open No. 51-68514 discloses that the crystallization process is carried out such that water is added to a reaction solution for aldol condensation to keep the total content of the HPA and/or the dimer thereof within the range of 23 to 30% by mass after distilling isobutyl aldehyde off from the reaction solution. However, when crystallization was carried out at such high concentrations after the reaction solution was cooled down to 15 to 20° C., it produces a slurry product with an extremely high viscosity or one without fluidity. Therefore, there arises a disadvantage that it is very difficult to be handled industrially. Further, Japanese Patent Application Laid-Open No. 51-68514 discloses that a large amount of the HPA and/or the dimer thereof remain/remains in a liquid obtained by the solid-liquid separation of the slurry, so the HPA and/or the dimer thereof can be recovered by extracting with isobutyl aldehyde and circulating an organic phase in the step of low-boiling distillation, while isobutyl aldehyde dissolved in an aqueous phase is also recovered by distillation. However, because of a large amount of isobutyl aldehyde distilled in a distillation column, it is energetically disadvantageous.

Further, Japanese Patent Publication No. 06-29206 discloses that part of filtrate and wash solutions obtained in the steps of solid-liquid separation and washing is circulated into an aldol condensation reactor and the distillation column, while the remaining part is subjected to a deamination processing to utilize it as addition water and rinse water in the crystallization process. In this case, however, formic acid, which is a by-product from the aldol condensation, is accumulated by circulation, causing a decrease in a pH level of the solution to be subjected to the crystallization. Therefore, there is a disadvantage in that the HPA and/or the dimer thereof are/is not easily crystallized. Further, even in the method of Japanese Patent Publication No. 06-29206, because a large amount of the liquid is circulated in the step of distillation, there are disadvantages in that the distillation step is highly loaded, it is energetically disadvantageous, and the steps are complicated since regeneration of the ion exchange resin used in a deamination processing is necessary.

SUMMARY OF THE INVENTION

An object of the present invention is to solve the problems described above, which are caused when an HPA-containing aqueous solution is diluted by addition of water and purified by crystallization, and to provide a method of efficiently and simply producing high-purity HPA and/or a dimer thereof in an industrially advantageous manner.

The present inventors have intensively studied to solve the above problems and attained the present invention by finally finding out a fact that high-purity HPA and/or the dimer thereof in high yield with facilitation of industrial-handling can be obtained via crystallization by adjusting a pH value of an aqueous solution, which contains the HPA and/or the dimer thereof obtained by distilling low boiling point components from a reaction mixture of isobutyl aldehyde and formaldehyde, and keeping the concentration(s) of the HPA and/or the dimer thereof and the concentration of the formaldehyde within an appropriate range.

In other words, the present invention provides a method of producing high-purity hydroxypivalaldehyde and/or a dimer thereof as described below.

1. A method of producing high-purity hydroxypivalaldehyde and/or dimer thereof, comprising: reacting isobutyl aldehyde with formaldehyde in a presence of a basic catalyst; distilling off the low boiling point component including unreacted isobutyl aldehyde to obtain an aqueous solution; adding a diluent to the aqueous solution; cooling the aqueous solution to crystallize at least one of the hydroxypivalaldehyde and the dimer thereof; and subjecting the aqueous solution to a solid-liquid separation, followed by washing with an organic solvent and/or water to obtain at least one of the high-purity hydroxypivalaldehyde and the dimer thereof, wherein the aqueous solution containing at least one of the hydroxypivalaldehyde and the dimer thereof obtained by distilling off the low boiling point component is diluted by adding the diluent and a basic compound, so that the concentration of at least one of the hydroxypivalaldehyde and the dimer thereof becomes 5 to 23% by mass, the concentration of formaldehyde becomes 0.2 to 2.5% by mass, and the pH value becomes 5.0 or more, then the solution is crystallized at a temperature of 20 to 45° C., consequently the crystal of at least one of the hydroxypivalaldehyde and the dimer thereof is subjected to the solid-liquid separation and washed.

2. A method of producing high-purity hydroxypivalaldehyde and/or dimer thereof according to the above item 1, in which at least one of the separation liquid from solid-liquid separation and a wash solution is used as the diluent.

3. A method of producing high-purity hydroxypivalaldehyde and/or dimer thereof according to the above item 2, in which the separation liquid from the solid-liquid separation is repeatedly used as the diluent two or more times.

4. A method of producing high-purity hydroxypivalaldehyde and/or dimer thereof according to any one of the above items 1 to 3, in which a crystal slurry obtained by the crystallization has a viscosity of 500 mPa·s or less.

In the production method of the present invention, handling of a high-viscosity slurry and carrying out any complicated operation such as regeneration of an ion exchange resin are not necessary, so the high-purity HPA and/or the dimer thereof can be obtained in high yield in an energetically advantageous manner. In addition, favorably, it can be industrially used as a synthetic intermediate of organic compounds such as neopentyl glycol, 2,2-dimethyl-1,3-propanediol hydroxypivalic acid monoester, hydroxypivalic acid, and spiroglycol.

Further, in the production method of the present invention, a repetitive use of the separation liquid from the solid-liquid separation improves the yield of the HPA and/or the dimer thereof while reducing the burden of wastewater treatment, so it can be further advantageous in terms of industrial use.

DETAILED DESCRIPTION OF THE INVENTION

The present invention relates to an improvement in the process of crystallization from an aqueous solution containing HPA and/or a dimer thereof (hereinafter, referred as "crude HPA aqueous solution") obtained by distilling off low boiling point components from a liquid produced by a reaction of isobutyl aldehyde with formaldehyde.

In the present invention, the crude HPA aqueous solution to be provided as a raw material for crystallization can be obtained by carrying out an aldol condensation of isobutyl aldehyde with formaldehyde in the presence of a basic catalyst, and then distilling off low boiling point components, such as unreacted isobutylaldehyde and formaldehyde, from a liquid produced by the aldol condensation. Formaldehyde used in the production of the crude HPA aqueous solution may be formaldehyde or an aqueous formaldehyde solution (formalin). However, the aldol condensation reaction of isobutyl aldehyde with formaldehyde, to which the basic catalyst is added, tends to be influenced extensively by the water concentration of a reaction system. When the concentration of isobutyl aldehyde or formaldehyde is low, the reaction rate becomes slow and a certain yield cannot be attained. Therefore, the formaldehyde concentration of formalin is preferred to be as high as possible. The raw material formalin is preferred to have a formaldehyde concentration of 37% by mass or more and contain no methanol or the least amount of methanol as possible.

For the isobutyl aldehyde used in the production of the crude HPA aqueous solution, any of those commercially available in the market may be used. Among those, preferable is one containing n-butyl aldehyde and the like as little as possible while the purity of an organic material is 99% or more.

In the present invention, the aldol condensation reaction of isobutyl aldehyde with formaldehyde may be of either a batch-wise type or a continuous type and may be preferably carried out under normal pressure or pressurized conditions and under airtight conditions or in a stream of nitrogen gas. In the case of the batch-wise type, there is no particular restriction to the procedures of supplying the isobutyl aldehyde, the formaldehyde (formalin), and the catalyst. In this case, however, when isobutyl aldehyde or formaldehyde (formalin) is previously brought into contact with a basic catalyst, the aldol condensation reaction or the Cannizzaro reaction of isobutyl aldehyde or formaldehyde by itself may occur and the yield of HPA and/or a dimer thereof may decrease. Thus, the method of supplying a basic catalyst into a mixture of isobutyl aldehyde and formaldehyde (formalin) is preferable. Further, in the case of the continuous type, there is no particular restriction to the procedures of supplying the isobutyl aldehyde, the formaldehyde (formalin), and the catalyst, but it is preferable to be carried out in a multistage process of about 2 to 4 stages to improve the efficiency of the reaction.

The molar equivalent of isobutyl aldehyde fed with respect to formaldehyde is typically in the range of 0.8 to 1.6, preferably 0.9 to 1.4. In the case of the batch-wise type, the reaction is heterogeneous for several minutes from the initiation of the reaction. Subsequently, the reaction turns to be homogeneous while producing HPA and/or a dimer thereof. Under normal pressure, the reaction temperature is typically 40 to 98° C., preferably 80 to 95° C. Under normal pressure, the reaction stops briefly at about 62 to 65° C., which is the reflux temperature of isobutyl aldehyde. Subsequently, as HPA and/or a dimer thereof are/is generated (consumption of isobutyl aldehyde), the reaction temperature gradually rises, and is finally controlled at 80° C. or above in general. The reaction can be completed when the temperature is kept at about 80 to 95° C. for about 0.05 to 2 hours. In the case of the continuous type, the reaction proceeds in a homogenous system. In general the reaction temperature is 50 to 98° C., preferably 70 to 95° C., and the retention time may be about 0.1 to 5 hours, preferably 0.3 to 3 hours. The reaction temperatures can be controlled by heating/cooling with a jacket, coil, or the like attached to a reactor, cooling by circulation of a reaction solution in an external heat exchanger, and removing heat by reflux of low boiling point components.

Examples of the basic catalyst used in the aldol condensation reaction include inorganic bases such as sodium hydroxide, potassium hydroxide, sodium carbonate, and potassium carbonate, and organic bases such as tertiary amine and pyridine. Among those, tertiary amine is preferably used because the yield may decrease due to the Cannizzaro reaction of HPA and/or a dimer thereof with unreacted formaldehyde, which occurs concurrently when the basicity is too strong, and the reaction becomes slow when the basicity is too weak. Examples of the tertiary amine include trimethylamine, triethylamine, tripropylamine, triisopropylamine, tributylamine, triisobutylamine, N-methyl piperidine, N-ethyl piperidine, N-methyl morpholine, N-ethyl morpholine, N-methylpyrrolidine, and N-ethyl pyrrolidine. Among those, trimethylamine, triethylamine, and a mixture thereof are preferable because each of them is available with low cost, and triethylamine is more preferable. A preferable addition amount of the basic catalyst may vary depending on the kind thereof, but typically is set at 0.001 to 0.5, preferably 0.01 to 0.2, in molar equivalent with respect to isobutyl aldehyde.

After such the aldol condensation reaction, low boiling point components such as unreacted isobutyl aldehyde, formaldehyde, or methanol which is contained in formalin as impurity, can be distilled off, thereby obtaining an aqueous solution containing HPA and/or a dimer thereof and water (crude HPA aqueous solution). A rise in temperature causes the HPA and/or the dimer thereof to denature quickly, so distillation of low boiling point components is preferably carried out at head temperatures of about 40 to 80° C. under reduced pressures of about 25 to 95 kPa, which do not affect the recovery of unreacted isobutyl aldehyde or the like. Further, the distillation process may be of a batch-wise type or a continuous type. For accelerating the removal of low boiling point components, the distillation may be carried out after the addition of water.

The resulting aqueous solution containing the HPA and/or the dimer thereof (crude HPA aqueous solution) is diluted with the addition of a diluent. Examples of the diluent include (a) dilution water, (b) a separation liquid produced by the solid-liquid separation, and (c) a wash solution obtained by washing crystals of the HPA and/or the dimer thereof with water, or an appropriate combination thereof. The total concentration of the HPA and/or the dimer thereof in the aqueous solution after the dilution is adjusted to 5 to 23% by mass. It is preferably adjusted to 15 to 22% by mass. By adjusting to such a range, the HPA and/or the dimer thereof can be industrially produced in a stable manner with high production efficiency. It is industrially preferable to adjust the total concentration of the HPA and/or the dimer thereof in the solution after the dilution to 5% by mass or more because the HPA and/or the dimer thereof are/is not precipitated at all, or even when the HPA and/or the dimer thereof are/is precipitated, a significant decrease in amount of production with respect to the capacity of a crystallization vessel does not occur.

Further, the liquid (b) obtained from the solid-liquid separation and the wash solution (c) contain a large amount of the HPA and/or the dimer thereof, so it is preferable to use the separation liquid used in the solid-liquid separation or the wash solution obtained when the high-purity HPA and/or a dimer thereof are/is prepared instead of dilution water.

The separation liquid used in the solid-liquid separation may be repeatedly used as diluent two or more times. The more repeatedly the separation liquid is used, the higher recovery rate of HPA and/or a dimer thereof and the lower burden of wastewater treatment are maintained. Further, the separation liquid used in the solid-liquid separation may be used as dilution water repeatedly, so the amount of a basic compound to be used as described below can be reduced and the burden of waste water treatment can be thus reduced. Therefore, the repetitive use of the separation liquid is industrially advantageous.

In the present invention, a basic compound is added to a crude HPA aqueous solution added with a diluent to adjust the pH value of the crude HPA aqueous solution. The basic compound is not particularly limited, but is preferably the same basic catalyst as one used in an aldol condensation reaction, more preferably, any of organic amines which can be used as a basic catalyst, and most preferably, tertiary amine. The pH value is adjusted to 5.0 or more, preferably 6.0 or more. It is industrially advantageous to adjust the pH value to 5.0 or more because the crystallization rate of HPA and/or a dimer thereof can be prevented from being significantly lowered. As described above, when a separation liquid produced by a solid-liquid separation or a wash solution is used as a diluent, it becomes possible to reduce the usage amount of the basic compound to be added since the basic compound is contained in the separation liquid or the wash solution.

Further, in the present invention, the concentration of formaldehyde in a crude HPA aqueous solution is adjusted to 0.2 to 2.5% by mass by the addition of a diluent. The formaldehyde has a characteristic of inhibiting the crystallization of HPA and/or a dimer thereof, and an extensive increase in the amount of formaldehyde causes an extensive decrease in crystallization rate of the HPA and/or the dimer thereof. Thus, the concentration of formaldehyde is adjusted to 0.2 to 2.5% by mass, preferably 0.2 to 2% by mass. It is industrially advantageous to adjust the concentration of formaldehyde to 2.5% by mass or less because there is no drastic decrease in both the crystallization amount and the crystallization rate of the HPA and/or the dimer even when the pH is adjusted to 5.0 or more. When a separation liquid, which is obtained in a solid-liquid separation using a crude HPA aqueous solution having a high formaldehyde concentration, is repeatedly used instead of dilution water, the unreacted formaldehyde is kept at a concentration of not more than 2.5% by mass.

If the formaldehyde concentration is lower than 0.2% by mass, no particular inconvenience in the crystallization of HPA and/or a dimer thereof occurs. However, as a method of lowering the concentration of formaldehyde to less than 0.2% by mass, there is a method of increasing the conversion rate of formaldehyde using an excess amount of isobutyl aldehyde at the time of the aldol condensation reaction. In this case, however, it is disadvantageous in terms of industrial operation because the condensation of isobutyl aldehyde itself occurs, thereby causing a decrease in yield of HPA and/or a dimer thereof. In addition, as another method of lowering the concentration of formaldehyde to less than 0.2% by mass, there is a method of increasing the removal rate of formaldehyde by raising the temperature of distillation while distilling low boiling point components off after an aldol condensation reaction. In this case, however, it is also industrially disadvantageous in that HPA and/or a dimer thereof are/is denatured to generate hydroxypivalate neopentylglycol monoester, thereby causing a decrease in yield of HPA and/or a dimer thereof.

The temperature of crystallization is preferably set in the range of 20 to 45° C., more preferably in the range of 28 to 43° C. Such a temperature range allows HPA and/or a dimer thereof to be stably crystallized at a high recover rate. It is advantageous in terms of industrial operation to adjust the temperature of crystallization to 20° C. or more so that viscosity of slurry becomes high or the slurry loses its fluidity, and an excess amount of a solution required for cooling becomes unnecessary. It is extensively advantageous in terms of industrial operation to adjust the temperature of crystallization to 45° C. or less because HPA and/or a dimer thereof can be crystallized in an appropriate amount.

For carrying out the crystallization while retaining the fluidity of slurry, it is preferable to complete the crystallization at a slurry viscosity of 500 mPa·s or less, more preferably 300 mPa·s or less at the aforementioned slurry temperatures. Therefore, it is advantageous in terms of operation for the solid-liquid separation to keep the slurry viscosity to 500 mPa·s or less. A device used for the solid-liquid separation is not particularly limited, but a basket-type centrifuge that can efficiently wash crystals can be preferably used.

The crystals of HPA and/or a dimer thereof thus separated are washed with an organic solvent and/or water, resulting in high-purity HPA and/or a dimer thereof. The organic solvent and/or water may be preferably used at about 0.2 to 5 parts by mass with respect to the crystal of the separated HPA and/or the dimer thereof.

For washing, the organic solvent and/or water may be used, but water is preferable. When water is used, a wash solution used for washing the crystals may be employed as a diluent for a crude HPA aqueous solution as described above. When the organic solvent is used, the kinds of the organic solvent are not particularly limited, but are preferably alcohols and ketones, which are polar solvents, because of their high washing effects. Among those, methanol, ethanol, propanol, and acetone, which can be miscible with water are preferable. The mixing ratio between the organic solvent and water is not particularly limited.

EXAMPLES

Hereinafter, the present invention will be described in more detail with reference to examples. However, the invention is not particularly limited to such examples. Further, in the following examples, the composition of a crude HPA aqueous solution was analyzed using gas chromatography.

[Method of Measuring the Viscosity of Slurry]

The viscosity of slurry was determined at a temperature of crystallization using a B-type viscometer (Type: BM, manufactured by Tokyo Keiki Seizosho Co., Ltd.).

[Method for Measurement by Gas Chromatography]

In a gas chromatographic analysis on HPA and/or a dimer thereof, a sample was prepared in an acetone solution using a capillary column (corresponding to DB-1 of Agilent Technologies). The HPA and/or the dimer thereof are/is evaluated as HPA in total.

Reference Example 1

An aldol condensation reaction was carried out by adding 9.9 parts by mass of triethylamine (highest quality, manufactured by Wako Pure Chemical Industries, Ltd.) as a catalyst to a mixture of 199.5 parts of isobutyl aldehyde (first grade, manufactured by Wako Pure Chemical Industries, Ltd.) and 225 parts by mass of 40-mass % formalin (manufactured by Mitsubishi Gas Chemical Company, Ltd.) while the mixture was stirred. The low boiling point components such as unreacted isobutyl aldehyde and triethylamine were distilled off from the reaction solution at 70 to 80° C. under a pressure of 40 kPa, thereby 425 parts by mass of a crude HPA aqueous solution was obtained. As a result of analyzing the composition of the crude HPA aqueous solution, the contents of the respective components were 62.1% by mass of HPA, 1.53% by mass of neopentyl glycol, 1.60% by mass of formaldehyde, 1.30% by mass of triethylamine, 0.41% by mass of formic acid, 0.95% by mass of hydroxypivalate neopentylglycol monoester, 28.5% by mass of water, and 3.65% by mass of other components.

Example 1

210 parts by mass of the crude HPA aqueous solution obtained in Reference Example 1 was added with 623 parts by mass of dilution water to adjust the concentration of HPA and/or a dimer thereof to 16.5% by mass. Further, 0.5 parts by mass of triethylamine serving as a pH regulator was added to the resulting mixture, attaining a pH value of 6.2. At this time, the concentration of formaldehyde was 0.40% by mass. This solution was stirred and cooled down to 40° C., and then crystallized at 39 to 40° C. After 90 minutes, the crystallization was completed. At this time, the viscosity of slurry was 85 mPa·s. Subsequently, a solid-liquid separation was carried out using a centrifugal separator and the resulting crystal (HPA and a dimer thereof) was then washed with 80 parts by mass of a wash solution. As a result, 780 parts by mass of a separation liquid was recovered and 75 parts by mass of a wet crystal was then obtained. The wet crystal was dried at 30° C. under a nitrogen stream, thereby obtaining 58.2 parts by mass of HPA and/or a dimer thereof (dried crystal). The recovery rate of the HPA and/or the dimer thereof was 44.1% by mass with respect to those in the crude HPA aqueous solution. The dried crystal was analyzed by gas chromatography, and as a result, the purity of the HPA and/or the dimer thereof was 98.8% (see Table 1). It should be noted that HPA in the table represents "HPA and/or a dimer thereof".

Example 2

Both 110 parts by mass of the crude HPA aqueous solution obtained in Reference Example 1 and 740 parts by mass of the separation liquid obtained in the solid-liquid separation of Example 1 as diluent were fed to make a concentration of HPA and/or a dimer thereof 17.8% by mass. Further, 0.2 parts by mass of triethylamine was added, resulting in a pH value of 6.2. At this time, the concentration of formaldehyde was 0.58% by mass. A crystallization process was carried out in a similar manner as in Example 1 and then completed after 80 minutes. The viscosity of slurry at this time was 125 mPa·s. As in the case of Example 1, solid-liquid separation by using a centrifugal separator, washing, and drying were carried out, thereby obtaining 57.5 parts by mass of a dry crystal (HPA and/or a dimer thereof) and 783 parts by mass of the separation liquid. The recovery rate of HPA and/or a dimer thereof in the additional crude HPA aqueous solution was 83.2% by mass. Then, HPA and/or a dimer thereof were/was analyzed using gas chromatography. As a result, a purity of the HPA and/or the dimer thereof was 98.8% (see Table 1).

Examples 3 to 19

An aqueous solution containing HPA and/or a dimer thereof was obtained as in the case of Example 2, using 110 parts by mass of the crude HPA aqueous solution obtained in Reference Example 1 and the separation liquid obtained in the solid-liquid separation of Example 2, thereby carrying out the same crystallization with a pH value of 6.2. Subsequently, the separation liquid obtained in the solid-liquid separation was used, and similarly, an aqueous solution containing HPA and/or a dimer thereof was obtained, followed by an adjustment of the pH value thereof to 6.2 to 6.3. The same crystallization operation was repeated 17 times.

Table 1 shows the pH, the concentration of HPA and/or a dimer thereof, the concentration of formaldehyde, a time period of crystallization, the viscosity of slurry, and the recovery rate and purity of HPA and/or a dimer thereof in a new additional crude HPA aqueous solution, at each time of the operations.

TABLE 1

| | Number of repetitive use of separation liquid | pH | Concentration (% by mass) HPA | Concentration (% by mass) Formaldehyde | Crystallization time (min.) | Slurry viscosity (mPa·s) | Recovery rate (% by mass) | Purity (% by mass) |
|---|---|---|---|---|---|---|---|---|
| Example 1 | 0 | 6.2 | 16.5 | 0.40 | 90 | 85 | 44.1 | 98.8 |
| Example 2 | 1 | 6.2 | 17.8 | 0.58 | 80 | 125 | 83.2 | 98.8 |
| Example 3 | 2 | 6.2 | 17.6 | 0.73 | 79 | 120 | 79.0 | 98.3 |
| Example 4 | 3 | 6.0 | 17.5 | 0.78 | 75 | 125 | 79.7 | 98.3 |
| Example 5 | 4 | 6.3 | 17.9 | 0.85 | 92 | 140 | 77.5 | 98.3 |
| Example 6 | 5 | 6.3 | 18.6 | 0.93 | 113 | 125 | 75.9 | 98.2 |
| Example 7 | 6 | 6.2 | 19.6 | 0.89 | 88 | 140 | 79.7 | 98.5 |
| Example 8 | 7 | 6.2 | 18.4 | 0.94 | 107 | 130 | 82.2 | 98.6 |
| Example 9 | 8 | 6.2 | 18.8 | 0.84 | 90 | 140 | 84.0 | 98.8 |
| Example 10 | 9 | 6.3 | 18.8 | 0.98 | 81 | 135 | 83.7 | 99.8 |
| Example 11 | 10 | 6.2 | 19.9 | 1.02 | 92 | 145 | 83.0 | 99.8 |
| Example 12 | 11 | 6.2 | 19.8 | 1.12 | 93 | 140 | 79.9 | 99.8 |
| Example 13 | 12 | 6.2 | 20.0 | 1.20 | 96 | 145 | 79.6 | 99.5 |
| Example 14 | 13 | 6.2 | 20.0 | 1.17 | 94 | 145 | 82.6 | 99.1 |
| Example 15 | 14 | 6.2 | 19.6 | 1.19 | 111 | 145 | 74.1 | 99.3 |
| Example 16 | 15 | 6.2 | 19.8 | 1.29 | 91 | 145 | 74.5 | 99.2 |
| Example 17 | 16 | 6.3 | 20.5 | 1.25 | 95 | 145 | 84.2 | 99.4 |
| Example 18 | 17 | 6.2 | 20.5 | 1.33 | 91 | 145 | 82.5 | 99.6 |
| Example 19 | 18 | 6.2 | 20.5 | 1.33 | 90 | 145 | 79.4 | 99.2 |

Comparative Example 1

A crystallization process was carried out in the same way as in Example 1, except that no triethylamine was added and no pH adjustment was made. The pH value was 4.5. After 90 minutes, the crystallization was completed. The viscosity of slurry was 100 mPa·s Subsequently, the reaction product was subjected to a solid-liquid separation and then dried, thereby obtaining 804 parts by mass of a filtrate and 40.8 parts by mass of HPA and/or a dimer thereof. The recovery rate of the HPA and/or the dimer thereof was 31.8% by mass, and the HPA and/or the dimer thereof was analyzed then using gas chromatography, resulting in a purity of 98.8% (see Table 2).

Comparative Example 2

The concentration of HPA was adjusted to 17.7% by mass by feeding 110 parts by mass of the crude HPA aqueous solution obtained in Reference Example 1 and 740 parts by mass of the filtrate recovered in Comparative Example 1. Triethylamine was not added and the pH value of the mixture was 4.4, and then the crystallization process was carried out in a similar manner. After 90 minutes, the crystallization was completed. The viscosity of slurry was 98 mPa·s. Subsequently, the resulting product was subjected to a solid-liquid separation and then dried, thereby obtaining 36.2 parts by mass of HPA and/or a dimer thereof. A recovery rate of HPA and/or a dimer thereof was 53.0% by mass. As a result of analysis using gas chromatography, the purity was 98.8%.

Comparative Examples 3 to 12

The same crystallization process as that of Comparative Example 2 was repeated 11 times using 110 parts by mass of the crude HPA aqueous solution obtained in Reference Example 1 and the recovered filtrate. Table 2 shows the pH, the concentration of HPA and/or a dimer thereof, the concentration of formaldehyde, a time period of crystallization, the viscosity of slurry, and the recovery rate and purity of the HPA and/or the dimer thereof in a new additional crude HPA aqueous solution, at each time of the operations.

TABLE 2

| | Number of repetitive use of separation liquid | pH | Concentration (% by mass) HPA | Concentration (% by mass) Formaldehyde | Crystallization time (min.) | Slurry viscosity (mPa·s) | Recovery rate (% by mass) | Purity (% by mass) |
|---|---|---|---|---|---|---|---|---|
| Comparative Example 1 | 0 | 4.5 | 16.5 | 0.40 | 90 | 100 | 31.8 | 98.8 |
| Comparative Example 2 | 1 | 4.4 | 17.7 | 0.42 | 90 | 98 | 53.0 | 98.8 |
| Comparative Example 3 | 2 | 4.3 | 18.4 | 0.45 | 90 | 70 | 49.2 | 99.1 |

TABLE 2-continued

|  | Number of repetitive use of separation liquid | pH | Concentration (% by mass) HPA | Concentration (% by mass) Formaldehyde | Crystallization time (min.) | Slurry viscosity (mPa·s) | Recovery rate (% by mass) | Purity (% by mass) |
|---|---|---|---|---|---|---|---|---|
| Comparative Example 4 | 3 | 4.2 | 17.4 | 0.55 | 90 | 45 | 47.3 | 99.1 |
| Comparative Example 5 | 4 | 4.2 | 17.9 | 0.60 | 90 | 55 | 48.2 | 98.6 |
| Comparative Example 6 | 5 | 4.1 | 18.0 | 0.59 | 90 | 50 | 46.9 | 98.9 |
| Comparative Example 7 | 6 | 4.1 | 18.0 | 0.62 | 90 | 50 | 45.4 | 98.3 |
| Comparative Example 8 | 7 | 4.1 | 18.4 | 0.64 | 90 | 55 | 46.1 | 98.8 |
| Comparative Example 9 | 8 | 4.0 | 18.4 | 0.72 | 90 | 55 | 49.2 | 98.3 |
| Comparative Example 10 | 9 | 4.0 | 18.1 | 0.70 | 90 | 50 | 44.4 | 98.3 |
| Comparative Example 11 | 10 | 4.0 | 17.9 | 0.72 | 90 | 50 | 45.9 | 97.7 |
| Comparative Example 12 | 11 | 3.9 | 18.1 | 0.74 | 90 | 65 | 44.1 | 97.7 |

In Table 2, when the crystallization was repeated without adjusting the pH, the pH value gradually decreased. In addition, the recovery rate of HPA and/or a dimer thereof and the purity decreased along with the decrease in pH value. In contrast, shown in Table 1, the crystallization carried out after the pH adjustment according to the present invention allows the purity and recovery rate to be kept at high levels even when the crystallization is repeated.

Comparative Example 13

A crystallization process was carried out in the same way as in Example 1, except that 312 parts by mass of water was added to 210 parts by mass of the crude HPA aqueous solution obtained in Reference Example 1 to adjust the concentration of HPA and/or a dimer thereof to 25.0% by mass. After 70 minutes from the initiation of crystallization, the viscosity of slurry increased to 1,000 mPa·s or more, thereby resulting in a loss of fluidity. Thus, the crystallization process was not able to proceed anymore.

Comparative Example 14

A crystallization process was carried out in the same way as in Example 1, except that a crystallization temperature was set to 50° C. After 180 minutes from the initiation of crystallization, no slurry was obtained and the solution stayed clear.

Reference Example 2

An aldol condensation reaction was carried out by adding 9.9 parts by mass of triethylamine as a catalyst to a mixture of 199.5 parts by mass of isobutyl aldehyde and 300 parts by mass of 40-mass % formalin while the mixture was stirred. From a reaction solution thus obtained, low boiling point components such as unreacted isobutyl aldehyde and triethylamine were distilled off at 70° C. under a pressure of 40 kPa, thereby obtaining 480 parts by mass of a crude HPA aqueous solution. As a result of analyzing the composition of the crude HPA aqueous solution, the contents of the respective components were 56.0% by mass of HPA, 1.50% by mass of neopentyl glycol, 7.50% by mass of formaldehyde, 0.95% by mass of triethylamine, 2.05% by mass of formic acid, 0.85% by mass of hydroxypivalate neopentylglycol monoester, 28.0% by mass of water, and 3.15% by mass of other components.

Example 20

210 parts by mass of the crude HPA aqueous solution obtained in Reference Example 2 was added with 503 parts by mass of water to adjust the concentration of HPA and/or a dimer thereof to 16.5% by mass. Further, 1.5 parts by mass of triethylamine serving as a pH regulator was added to the resulting mixture, attaining a pH value of 6.1. At this time, the concentration of formaldehyde was 2.21% by mass. This solution was stirred and cooled down to 40° C., and then crystallized at 39 to 40° C. After 90 minutes, the crystallization was completed. At this time, the viscosity of slurry was 140 mPa·s. Subsequently, a solid-liquid separation was carried out using a centrifugal separator. At this time, 80 parts of water was used for washing a cake. As a result, 748 parts by mass of a filtrate was recovered and 61 parts by mass of the cake was then obtained. The cake was dried at 30° C. under a nitrogen stream, thereby obtaining 47 parts by mass of HPA and/or a dimer thereof. The recovery rate of HPA and/or a dimer thereof was 40.0% by mass, and the HPA and/or the dimer thereof were/was then analyzed by gas chromatography. As a result, the purity thereof was 98.6%.

Comparative Example 15

The concentration of HPA was adjusted to 18.0% by mass by feeding 110 parts by mass of the crude HPA aqueous solution obtained in Reference Example 2 and 740 parts by mass of the filtrate recovered in Example 20. The mixture was added with 1.5 parts by mass of triethylamine as a pH regulator to adjust the pH value to 6.1. At this time, the concentration of formaldehyde was 2.89% by mass. Subsequently, a crystallization process was carried out in the same way as in Example 20. The viscosity of slurry was 70 mPa·s. Subsequently, the resulting product was subjected to a solid-liquid separation and then dried, thereby obtaining 25 parts by mass of HPA and/or a dimer thereof. A recovery rate of HPA and/or a dimer thereof was 40.5% by mass. As a result of analysis using gas chromatography, the purity was 97.8%.

Reference Example 3

An aldol condensation reaction was carried out in the same way as in Reference Example 1. Subsequently, the resulting reaction solution was subjected to distillation to distill off low boiling point components, such as unreacted isobutyl aldehyde and triethylamine, at 100 to 105° C. under normal pressure, thereby obtaining 425 parts of the crude HPA aqueous solution. From the analysis of the composition of the crude HPA aqueous solution, the contents of the respective components were 50.1% by mass of HPA, 6.53% by mass of neopentyl glycol, 0.37% by mass of formaldehyde, 1.54% by mass of triethylamine, 1.81% by mass of formic acid, 7.50% by mass of hydroxypivalate neopentylglycol monoester, 28.5% by mass of water, and 3.77% by mass of other components.

Comparative Example 16

210 parts by mass of the crude HPA aqueous solution obtained in Reference Example 3 was added with 428 parts by mass of water to adjust the concentration of HPA and/or a dimer thereof to 16.5% by mass. Further, 1.3 parts by mass of triethylamine was added as a pH regulator to the mixture to adjust the pH value to 6.1. At this time, the concentration of formaldehyde was 0.12% by mass. The resulting solution was stirred while being cooled down to 40° C. Subsequently, the crystallization was carried out at 39 to 40° C. After 90 minutes, the crystallization was completed. At this time, the viscosity of slurry was 50 mPa·s. Subsequently, a solid-liquid separation was carried out using a centrifugal separator. At this time, 80 parts by mass of water was used for washing a cake. As a result, 763 parts by mass of a filtrate was recovered and 45 parts by mass of the cake was then obtained. The cake was dried at 30° C. under a nitrogen stream, thereby obtaining 33.3 parts by mass of HPA and/or a dimer thereof. The recovery rate of HPA and/or a dimer thereof was 31.7% by mass.

What is claimed is:

1. A method of producing high-purity hydroxypivalaldehyde and/or dimer thereof, comprising:
    reacting isobutyl aldehyde with formaldehyde in a presence of a basic catalyst;
    distilling off a low boiling point component including unreacted isobutyl aldehyde to obtain an aqueous solution;
    adding a diluent to the aqueous solution;
    cooling the aqueous solution to crystallize at least one of the hydroxypivalaldehyde and the dimer thereof; and
    subjecting the aqueous solution to a solid-liquid separation, followed by washing with an organic solvent and/or water to obtain at least one of the high-purity hydroxypivalaldehyde and the dimer thereof, wherein the aqueous solution containing at least one of the hydroxypivalaldehyde and the dimer thereof obtained by distilling the low boiling point component off is diluted by adding the diluent and a basic compound, so that the concentration of at least one of the hydroxypivalaldehyde and the dimer thereof becomes 5 to 23% by mass, the concentration of formaldehyde becomes 0.2 to 2.5% by mass, and the pH value becomes 5.0 or more, then the solution is crystallized at a temperature of 20 to 45° C., consequently the crystal of at least one of the hydroxypivalaldehyde and the dimer thereof is subjected to the solid-liquid separation and washed.

2. A method of producing high-purity hydroxypivalaldehyde and/or dimer thereof according to claim 1, wherein at least one of a separation liquid from solid-liquid separation and a wash solution is used as the diluent.

3. A method of producing high-purity hydroxypivalaldehyde and/or dimer thereof according to claim 2, wherein the separation liquid from the solid-liquid separation is repeatedly used as the diluent two or more times.

4. A method of producing high-purity hydroxypivalaldehyde and/or dimer thereof according to claim 1, wherein a crystal slurry obtained by the crystallization has a viscosity of 500 mPa·s or less.

5. A method of producing high-purity hydroxypivalaldehyde and/or dimer thereof according to claim 2, wherein a crystal slurry obtained by the crystallization has a viscosity of 500 mPa·s or less.

6. A method of producing high-purity hydroxypivalaldehyde and/or dimer thereof according to claim 3, wherein a crystal slurry obtained by the crystallization has a viscosity of 500 mPa·s or less.

7. A method of producing high-purity hydroxypivalaldehyde and/or dimer thereof according to claim 1, wherein said diluent is selected from the group consisting of water, a separation liquid produced by the solid-liquid separation, and a wash solution obtained by said washing to obtain at least one of the high-purity hydroxypivalaldehyde and the dimer thereof.

8. A method of producing high-purity hydroxypivalaldehyde and/or dimer thereof according to claim 1, wherein said diluent and the basic compound are added so that said concentration of the at least one of hydroxypivalaldehyde and the dimer thereof becomes 15 to 22% by mass.

9. A method of producing high-purity hydroxypivalaldehyde and/or dimer thereof according to claim 1, wherein said basic compound is an organic amine.

10. A method of producing high-purity hydroxypivalaldehyde and/or dimer thereof according to claim 9, wherein said organic amine is a tertiary amine.

11. A method of producing high-purity hydroxypivalaldehyde and/or dimer thereof according to claim 1, wherein said diluent and said basic compound are added so that said pH value becomes 6.0 or more.

12. A method of producing high-purity hydroxypivalaldehyde and/or dimer thereof according to claim 1, wherein said diluent and said basic compound are added so that the concentration of formaldehyde becomes 0.2 to 2.0% by mass.

13. A method of producing high-purity hydroxypivalaldehyde and/or dimer thereof according to claim 1, wherein the solution is crystallized at a temperature of 28 to 43° C.

14. A method of producing high-purity hydroxypivalaldehyde and/or dimer thereof according to claim 4, wherein a crystal slurry obtained by the crystallization has a viscosity of 300 mPa·s or less.

* * * * *